US010426444B2

(12) United States Patent
Akiyama (10) Patent No.: US 10,426,444 B2
(45) Date of Patent: Oct. 1, 2019

(54) ULTRASONIC DIAGNOSIS APPARATUS, MEDICAL IMAGE PROCESSING APPARATUS AND MEDICAL IMAGE PROCESSING METHOD

(71) Applicant: Toshiba Medical Systems Corporation, Otawara-shi (JP)

(72) Inventor: Mitsuo Akiyama, Otawara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 703 days.

(21) Appl. No.: 14/732,251

(22) Filed: Jun. 5, 2015

(65) Prior Publication Data

US 2015/0265255 A1 Sep. 24, 2015

Related U.S. Application Data

(63) Continuation of application No. PCT/JP2013/084515, filed on Dec. 24, 2013.

(30) Foreign Application Priority Data

Dec. 21, 2012 (JP) ................................. 2012-279562

(51) Int. Cl.
*A61B 8/00* (2006.01)
*A61B 8/06* (2006.01)
(Continued)

(52) U.S. Cl.
CPC .............. *A61B 8/585* (2013.01); *A61B 8/06* (2013.01); *A61B 8/14* (2013.01); *A61B 8/461* (2013.01);
(Continued)

(58) Field of Classification Search
None
See application file for complete search history.

(56) References Cited

U.S. PATENT DOCUMENTS 5,331,419 A * 7/1994 Yamada ............... G01B 11/024
   348/137
6,817,982 B2 * 11/2004 Fritz .................... A61B 8/0858
   382/128
(Continued)

FOREIGN PATENT DOCUMENTS

JP   04-282142 A   10/1992
JP   07-039546 A    2/1995
(Continued)

OTHER PUBLICATIONS

International Search Report dated Feb. 25, 2014 in PCT/JP2013/084515 filed Dec. 24, 2013.
(Continued)

*Primary Examiner* — Katherine L Fernandez
(74) *Attorney, Agent, or Firm* — Oblon, McClelland, Maier & Neustadt, L.L.P.

(57) ABSTRACT

An ultrasonic diagnosis apparatus according to one embodiment includes an ultrasonic probe, an image generating processor, a monitor, a database, and a calibration information generation processor. The image generating processor generates an ultrasonic image, based on an echo signal obtained through the ultrasonic probe. The monitor displays the ultrasonic image. The database stores image data including the ultrasonic image displayed on a screen of the monitor. The calibration information generation processor generates calibration information including a conversion value for performing a predetermined measurement with respect to the ultrasonic image included in the image data, based on the database storing image data including the ultrasonic image displayed on a screen of the monitor, and a positional relationship between at least one scale mark existing in the image data and the ultrasonic image.

14 Claims, 8 Drawing Sheets

(51) Int. Cl.
*A61B 8/08* (2006.01)
*A61B 8/14* (2006.01)
(52) U.S. Cl.
CPC .............. *A61B 8/488* (2013.01); *A61B 8/463* (2013.01); *A61B 8/467* (2013.01); *A61B 8/5207* (2013.01)

(56) References Cited

U.S. PATENT DOCUMENTS

| | | | |
|---|---|---|---|
| 9,158,986 B2 * | 10/2015 | Nakamura | ............. G06K 9/344 |
| 2013/0259363 A1 * | 10/2013 | Ozawa | ................ G06K 9/4652 |
| | | | 382/164 |

FOREIGN PATENT DOCUMENTS

| | | |
|---|---|---|
| JP | 2000-262532 A | 9/2000 |
| JP | 2004-229924 A | 8/2004 |
| JP | 2005-081082 A | 3/2005 |
| JP | 2009-261520 A | 11/2009 |

OTHER PUBLICATIONS

International Written Opinion dated Feb. 25, 2014 in PCT/JP2013/084515 filed Dec. 24, 2013 with English translation.

* cited by examiner

ULTRASONIC DIAGNOSIS APPARATUS, MEDICAL IMAGE PROCESSING APPARATUS AND MEDICAL IMAGE PROCESSING METHOD

CROSS-REFERENCE TO RELATED APPLICATIONS

This application is a Continuation Application of PCT Application No. PCT/JP2013/084515, filed Dec. 24, 2013 and based upon and claiming the benefit of priority from Japanese Patent Application No. 2012-279562, filed Dec. 21, 2012 the entire contents of all of which are incorporated herein by reference.

FIELD

Embodiments of the present invention relate to an ultrasonic diagnosis apparatus, a medical image processing apparatus and a medical image processing method.

BACKGROUND

An ultrasonic diagnosis apparatus is a diagnosis apparatus which displays an image of intravital information. Compared to other image diagnosis apparatuses such as an X-ray diagnosis apparatus and an X-ray computed tomography apparatus, the ultrasonic diagnosis apparatus is inexpensive and is free from exposure, and is utilized as a useful apparatus for observation in real time in a non-invasive manner. The range of applications of the ultrasonic diagnosis apparatus is wide, and the ultrasonic diagnosis apparatus is applied to diagnosis of a circulatory organ such as the heart, the abdominal region such as the liver and kidney, peripheral blood vessels, obstetrics and gynecology, and breast cancer.

In the meantime, in the ultrasonic diagnosis apparatus, an ultrasonic image, which is obtained by transmitting/receiving ultrasonic to/from a subject by using an ultrasonic probe, is displayed on a monitor. The ultrasonic diagnosis apparatus includes a function of storing (saving) the image data, which is displayed on the screen of the monitor, in a database as still images or a moving picture.

In some cases, calibration information (information relating to a living body, and setting information of the system) is set as additional information for the image data stored in the database, for an occasion of measuring an intravital conversion distance or a blood flow velocity by using this image data. In the case where the image data, for which the calibration information is set, is displayed, each of locations on the ultrasonic image can be measured.

On the other hand, for example, in order to rearrange cases on a personal computer, it is possible to remove the calibration information from the image data stored in the database, and to output only the image data in a format which enables read-out on the personal computer (e.g. bitmap format, JPEG format, AVI format, MPEG format).

Furthermore, if the calibration information is set, the amount of data increases. Thus, in some cases, the image data is stored in the database in a state in which the calibration information is not set.

In the meantime, when image data, for which the calibration information is set, is displayed as described above, a predetermined measurement process cannot be executed on the ultrasonic image.

For example, if an operator tries to perform measurement by himself/herself in the state in which such image data is displayed, the operator will count, for instance, scale marks (e.g. pixel intervals) or the like on the screen by himself/herself, collates them with corresponding indices of length and perform calibration, and will then estimate an actual size, etc. In this case, a great deal of time and labor is required, and it is possible that the result is not accurate.

In addition, in the ultrasonic diagnosis apparatus, since a plurality of images can be displayed at the same time on one screen, it is very time-consuming to perform the above-described work for each image displayed on the screen, and more time and labor will be needed.

Thus, the object of the present invention is to provide an ultrasonic diagnosis apparatus and a medical image processing apparatus, which can automatically generate calibration information from image data.

DESCRIPTION OF EMBODIMENTS

Detailed Description

An ultrasonic diagnostic apparatus disclosed by this embodiment comprises; an ultrasonic probe, an image generating processor configured to generate an ultrasonic image, based on an echo signal which is obtained through the ultrasonic probe, a monitor configured to display the ultrasonic image, a memory configured to store image data including the ultrasonic image displayed on a screen of the monitor, and a calibration information generation processor configured to generate calibration information including a conversion value for performing a predetermined measurement with respect to the ultrasonic image included in the image data, based on a positional relationship between at least one scale mark existing in the image data and the ultrasonic image.

Embodiments will be described hereinafter with reference to the accompanying drawings. Incidentally, in a first embodiment and a second embodiment below, an example of application to an ultrasonic diagnosis apparatus is described. However, the embodiments are not limited to this example, and a generation method of calibration information, which will be described in each embodiment, is also applicable to various medical image diagnosis apparatuses such as an X-ray computed tomography apparatus, a magnetic resonance imaging apparatus, an X-ray diagnosis apparatus and a nuclear medicine diagnosis apparatus, or to a medical image processing apparatus for, for example, observing a medical image captured by various medical image diagnosis apparatuses.

(First Embodiment)

Figure 1:
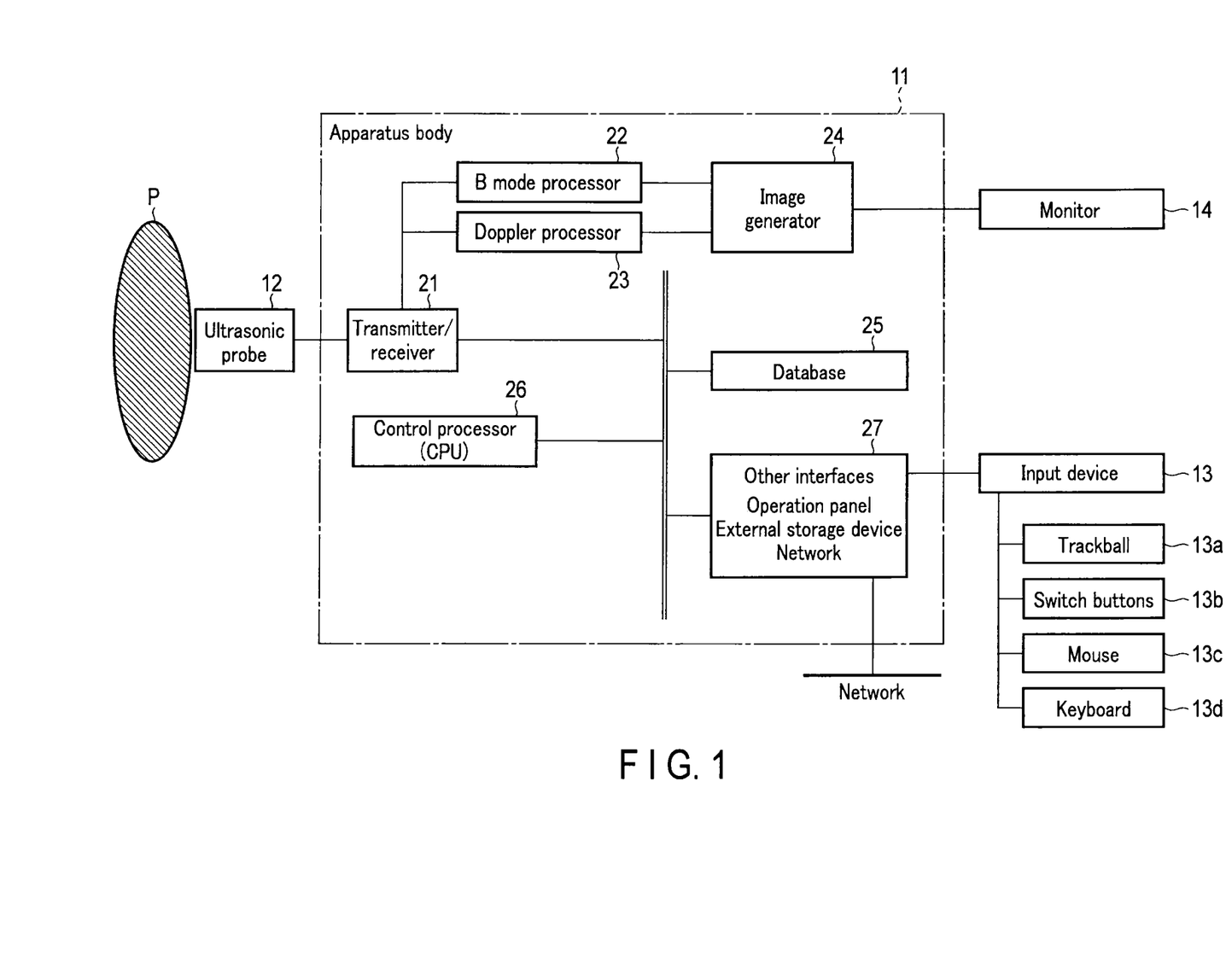
FIG. 1 is a view illustrating a block configuration of an ultrasonic diagnosis apparatus according to an embodiment.

FIG. 1 is a view illustrating a block configuration of an ultrasonic diagnosis apparatus according to the present embodiment. As illustrated in FIG. 1, the ultrasonic diagnosis apparatus includes an ultrasonic diagnosis apparatus body (hereinafter, simply referred to as "apparatus body") 11, an ultrasonic probe 12, an input device 13, and a monitor 14. In addition, the apparatus body 11 includes a transmitter/receiver 21, a B mode processor 22, a Doppler processor 23, an image generator 24, a database 25, a control processor (CPU) 26, and an interface unit 27. Incidentally, the transmitter/receiver unit 21, etc. included in the apparatus body 11 may be configured as hardware such as integrated circuits, or may be configured as software programs which are implemented as software modules. The functions of the respective structural elements will be described below.

The ultrasonic probe 12 includes a plurality of piezoelectric transducers which generate ultrasonic waves, based on a driving signal from the transmitter/receiver 21, and convert reflective waves from a subject P to electric signals; a matching layer provided on the piezoelectric transducers; and a backing member which prevents backward propagation of ultrasonic waves from the piezoelectric transducers. If ultrasonic waves are transmitted from the ultrasonic probe 12, the ultrasonic waves are successively reflected by discontinuous planes of acoustic impedance of intravital tissues, and are received by the ultrasonic probes 12 as an echo signal. The amplitude of this echo signal depends on a difference of the acoustic impedance in the discontinuous planes at which the reflection occurred. In addition, an echo in a case where transmitted ultrasonic pulses were reflected by a moving blood flow or by the wall of the heart, etc. undergoes frequency deviation, depending on a velocity component in an ultrasonic transmission direction of a moving body by a Doppler effect.

The input device 13 includes a trackball 13a, various switch buttons 13b, a mouse 13c and a keyboard 13d for inputting to the apparatus body 11 various instructions from the operator, conditions, a region-of-interest (ROI) setting instruction, various image quality condition setting instructions, etc.

The monitor 14 displays intravital morphological information and blood flow information as images, based on a video signal from the image generator 24.

The transmitter/receiver 21 includes a pulse generator, a transmission delay unit and a pulser, which are not shown. The pulse generator repeatedly generates rate pulses for forming ultrasonic waves at a predetermined rate frequency fr Hz (cycle; 1/fr second). The transmission delay unit imparts to a rate pulse of each channel a delay time which is necessary for focusing ultrasonic waves in a beam shape for each channel and for determining directivity of transmission. The pulser applies a driving pulse to the ultrasonic probe 12 at a timing based on the rate pulse for each channel.

In addition, the transmitter/receiver 21 includes a pre-amplifier, a reception delay unit and an adder, which are not shown. The pre-amplifier amplifies an echo signal, which was taken in through the ultrasonic probe 12, for each channel. The reception delay unit imparts a delay time, which is necessary for determining directivity of reception, to the amplified echo signal, and then executes an addition process in the adder. By this addition, a reflected component from a direction corresponding to the directivity of reception of the echo signal is emphasized, and a comprehensive beam of ultrasonic transmission/reception is formed by the reception directivity and transmission directivity.

The B mode processor 22 executes a B mode process on the echo signal from the transmitter/receiver 21. Specifically, the B mode processor 22 executes envelope detection of the echo signal from the transmitter/receiver 21, and executes logarithmic compression of the envelope-detected echo signal. Thereby, the B mode processor 22 generates data of a B mode image which represents the intensity of the echo signal by luminance. The generated data of the B-mode image is supplied to the image generator 24.

The Doppler processor 23 executes a Doppler process on the echo signal from the transmitter/receiver 21, and generates data of a Doppler spectrum image (an image of a Doppler mode) in a range gate. Specifically, the Doppler processor 23 executes orthogonal detection of the echo signal from the transmitter/receiver 21. The Doppler processor 23 extracts a signal in a preset range gate from the orthogonal-detected echo signal. The Doppler processor 23 executes spectrum analysis of the signal in the range gate by FFT (Fast Fourier Transform), and calculates a flow velocity value (flow velocity spectrum). The Doppler processor 23 generates data of a Doppler spectrum image which is indicative of a variation with time of the flow velocity spectrum. The generated data of the Doppler spectrum image is supplied to the image generator 24. Incidentally, for example, a color Doppler mode process for generating data of a color Doppler image may be executed on the echo signal from the transmitter/receiver 21.

The image generator 24 is composed of a DSC (Digital Scan Converter). The image generator 24 converts the data of the B mode image from the B mode processor 22 to image data which can be displayed on the monitor 14. Similarly, the image generator 24 converts the data of the Doppler spectrum image from the Doppler processor 23 to image data which can be displayed on the monitor 14.

In the meantime, in the present embodiment, the image data (display image data on the monitor 14) including the ultrasonic image displayed on the screen of the above-described monitor 14 is stored (accumulated) in the database 25, and can be accessed by the operator, for example, after diagnosis. In the ultrasonic diagnosis apparatus, there is a case in which a plurality of ultrasonic images are simultaneously displayed on one screen, and a plurality of ultrasonic images, for example, may be included in the image data stored in the database 25. In addition, it is assumed that, in the image data stored in the database 25, numerical values or scale marks for representing an intravital conversion distance, etc. in the ultrasonic image included in the image data are depicted (embedded).

Incidentally, in the present embodiment, image data, for which information that is used when a predetermined measurement is executed on an ultrasonic image is not set as additional information, may be stored in the database 25. Here, the additional information refers to, for example, information relating to a living body, such as depth of field, information as to how many ultrasonic images are included (displayed) in the image data and in what combination of modes (e.g. B mode, Doppler mode) the ultrasonic images are included, or information of a conversion value per pixel, etc. in the ultrasonic image.

The control processor 26 includes a function as an information processing device (computer), and controls the operation of the apparatus body 11. The control processor 26 reads out, for example, a control program for executing an image process, etc. (to be described later) from an internal storage device (not shown), and executes arithmetic operations, control, etc. relating to various processes. Incidentally, the details of the processes, which are executed by the control processor 26, will be described later.

The interface unit 27 is an interface relating to the input device 13, a network, and a new external storage device (not shown). The data, analysis results, etc. of the ultrasonic images, etc. obtained in the ultrasonic diagnosis apparatus can be transferred to other devices by the interface unit 27 over the network.

Figure 2:
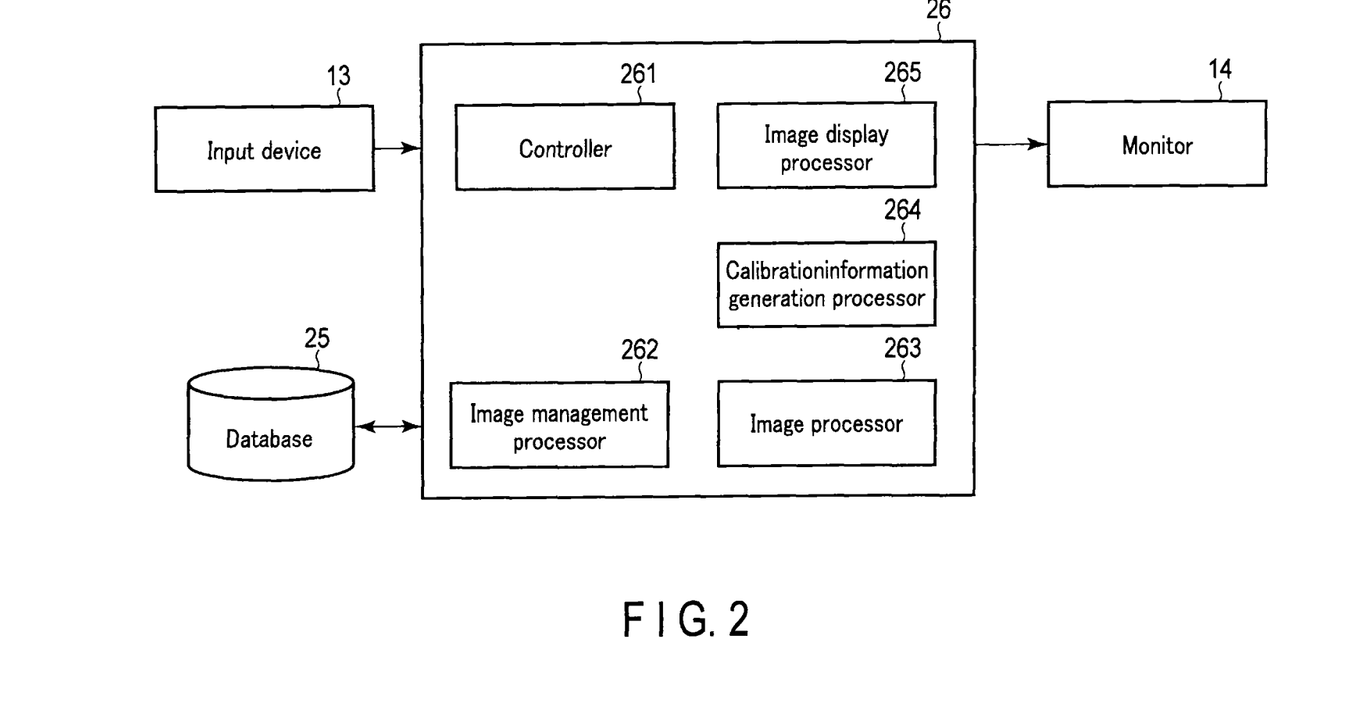
FIG. 2 is a block diagram which mainly illustrates a functional configuration of a control processor 26 shown in FIG. 1.

Next, referring to FIG. 2, a description is given of a process which is executed by the control processor 26 illustrated in FIG. 1. As illustrated in FIG. 2, the control processor 26 includes a controller 261, an image management processor 262, an image processor 263, a calibration information generation processor 264, and an image display processor 265. It is assumed that these components 261 to 265 are realized by the control processor 26 executing the above-described control program.

Based on an operation of an operator for selecting arbitrary image data from among image data stored in the database 25, the controller 261 instructs the image management processor 262 to read out the image data, which was selected by the operator, from the database 25. Incidentally, the operation for selecting arbitrary image data can be performed, for example, by using the input device 13.

In accordance with an instruction from the controller 261, the image management processor 262 reads out the image data, which was selected by the operator, from the database 25. The image data, which was read out of the database 25, is temporarily stored in the inside of the image management processor 262.

The image processor 263 determines whether additional information is set for the image data that was read out of the database 25 by the image management processor 262. If additional information is not set, the image processor 263 acquires the image data which is temporarily stored in the image management processor 262, and delivers the image data to the calibration data generation processor 264. On the other hand, if additional information is set, the image data, which is temporarily stored in the image management processor 262, is delivered to the image display processor 265 and displayed on the monitor 14.

Based on a plurality of numerical values existing in the image data delivered from the image management processor 262 and the positions of a plurality of scale marks existing near the respective numeral values, the calibration information generation processor 264 generates calibration information including a conversion value (hereinafter referred to as "calibration value") per pixel in an ultrasonic image included in the image data. When a plurality of ultrasonic images are included in the image data delivered from the image management processor 262, the calibration information generation processor 264 generates the calibration information for each image. The calibration information generation processor 264 sets the generated calibration information in the inside of the image management processor 262 as the additional information of the image data delivered from the image management processor 262.

The image display processor 265 displays on the monitor 14 the image data selected by the operator (the image data read out of the database 25). At this time, the image display processor 265 displays the calibration information, which was set as the additional information of the image data selected by the operator, together with the image data.

Figure 3:
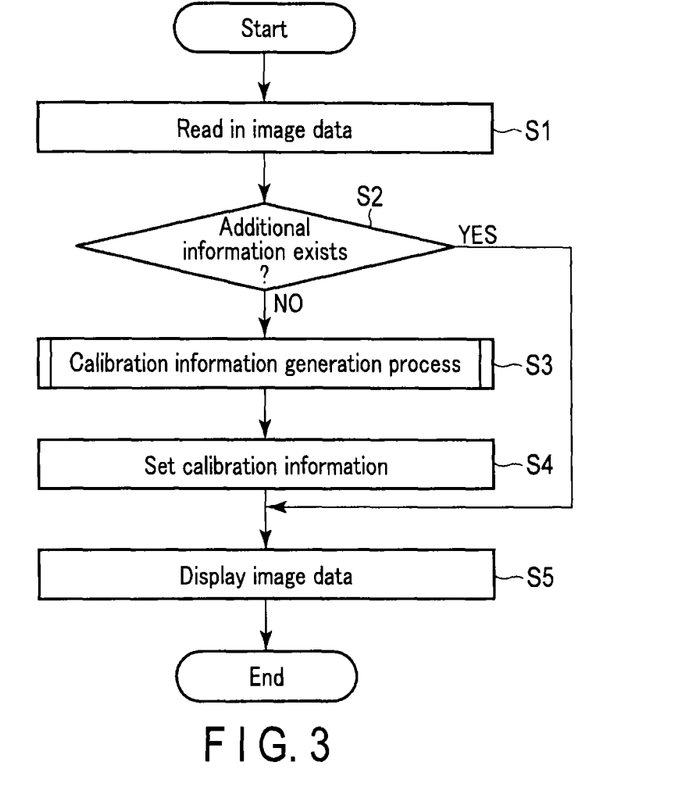
FIG. 3 is a flowchart illustrating a process procedure of the ultrasonic diagnosis apparatus according to the embodiment.

Next, referring to a flowchart of FIG. 3, a description is given of a process procedure of the ultrasonic diagnosis apparatus according to the present embodiment. Here, a description is given of a process at a time of generating the above-described calibration information from the image data stored in the database 25. Incidentally, the image data stored in the database 25 is image data at a time when an ultrasonic image was displayed on the screen of the monitor 14, as described above, and includes at least one ultrasonic image.

As described above, the operator can select desired image data from among a list of image data stored in the database 25, by operating the input device 13. Hereinafter, the image data selected by the operation is referred to as "selected image data".

In this case, the controller 261 receives operation information from the input device 13, and instructs the image management processor 262 to read in the selected image data.

Next, in accordance with the instruction from the controller 261, the image management processor 262 reads in the selected image data from the database 25 (step S1). At this time, the image management processor 262 temporarily stores the selected image data, which was read in from the database 25, in the inside of the image management processor 262. In addition, the image management processor 262 delivers the selected image data to the image display processor 265, and delivers to the image processor 263 information of the memory (e.g. address) in which the selected image data is temporarily stored.

For example, referring to the database 25, the image processor 263 determines whether additional information exists (i.e. additional information is set) for the selected image data (step S2). Incidentally, the additional information is information which is used when a predetermined measurement is executed for an ultrasonic image included in the selected image data, and is, for instance, information relating to a living body or setting information of the system.

Here, when no additional information exists for the selected image data, a predetermined measurement process cannot be executed for the ultrasonic image included in the selected image data. In other words, in order to execute a predetermined measurement process on the ultrasonic image included in the selected image data, it is necessary to set (generate) calibration information which is used in this measurement process.

Thus, when it has been determined that the additional information does not exist for the selected image data (NO in step S2), the image processor 263 acquires the selected image data, which is temporarily stored in the inside of the image management processor 262, by using the information delivered from the image management processor 262, in order to generate calibration information, and delivers this selected image data to the calibration information generation processor 264.

Next, based on the selected image data delivered from the image processor 263, the calibration information generation processor 264 executes a process (hereinafter referred to as "calibration information generation process") for generating calibration information which is used to measure, for example, an intravital conversion distance, blood flow velocity, etc. (step S3). The calibration information generated here includes, for example, a conversion value (calibration value) per pixel in the ultrasonic image included in the selected image data. Incidentally, the details of the calibration information generation process will be described later.

When the calibration information generation process has been executed, the calibration information generation processor 264 sets the generated calibration information as the additional information in the inside of the image management processor 262 (step S4).

In addition, in order to cause the generated calibration information to be displayed, the calibration information generation processor 264 delivers to the image display processor 265 information in which the calibration value included in the calibration information is converted to a character string (i.e. a character string representing the calibration value).

The image display processor 265 displays on the monitor 14 the selected image data which was delivered from the image management processor 262, for example, in accordance with an instruction from the controller 261 (step S5). Here, the information (the character string representing the calibration value), which was delivered from the calibration information generation processor 264, is displayed on the monitor 14 together with the selected image data.

On the other hand, when it has been determined in the above-described step S2 that the additional information exists, the process of step S3 and S4 is not executed, and the process of step S5 is executed.

By the execution of the above-described process, even with respect to the image data stored in the database 25 in the state in which no additional information is set, calibration information can automatically be generated and the calibration information can be set as additional information.

Figure 4:
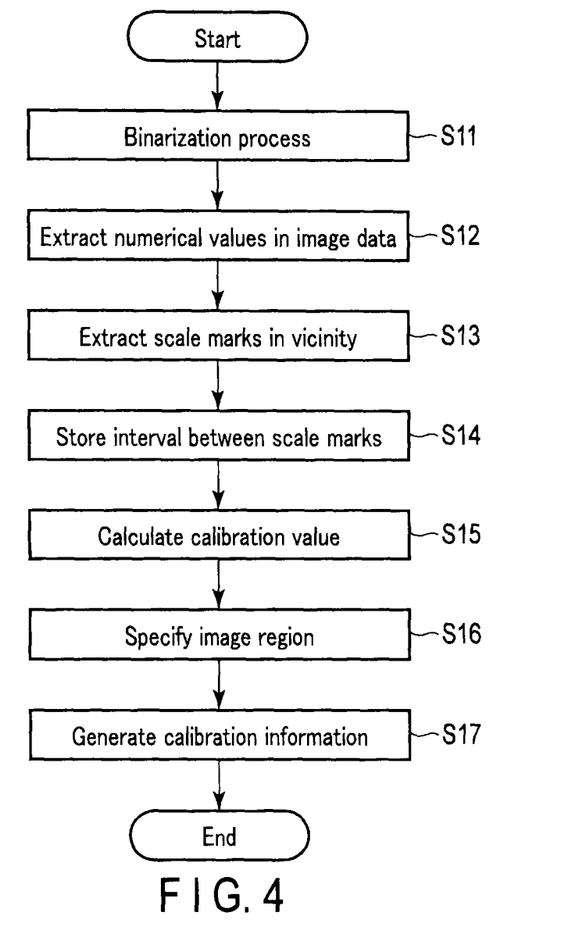
FIG. 4 is a flowchart illustrating a process procedure of a calibration information generation process.

Next, referring to a flowchart of FIG. 4, a description is given of a process procedure of the above-described calibration information generation process (the process of step S3 illustrated in FIG. 3).

To start with, the calibration information generation processor 264 acquires the selected image data delivered from the image processor 263 (that image data, among the image data stored in the database 25, which was selected by the operator). In the meantime, as described above, the numerical values (character string) and scale marks for representing, for example, the intravital conversion distance in the ultrasonic image included in the selected image data are depicted in the selected image data.

Next, the calibration information generation processor 264 executes a binarization process on the acquired selected image data (step S11). This binarization process is executed based on luminance which can distinguish the ultrasonic image included in the image data and the character string, such as numerical values, and scale marks.

The calibration information generation processor 264 extracts numerical values existing in the selected image data which was subjected to the binarization process (step S12).

Specifically, the calibration information generation processor 264 extracts a numerical value group arranged in a row in an X-axis direction (horizontal direction) (hereinafter referred to as "X-axis directional numerical value group") in the selected image data which was subjected to the binarization process. Similarly, the calibration information generation processor 264 extracts a numerical value group arranged in a row in a Y-axis direction (vertical direction) (hereinafter referred to as "Y-axis directional numerical value group") in the selected image data which was subjected to the binarization process. If the intervals of the extracted numerical values are equal, it is highly possible that these numerical values are numerical values for representing, for example, the intravital conversion distance. Incidentally, a plurality of X-axis directional numerical value groups and Y-axis directional numerical value groups may be extracted.

Next, the calibration information generation processor 264 extracts a scale mark near the extracted numerical values, in the selected image data which was subjected to the binarization process (step S13). In this case, a predetermined mark disposed at a nearest position in the up-and-down direction or left-and-right direction of the numeral values is extracted as a scale mark.

Specifically, the calibration information generation processor 264 extracts a scale mark group existing at regular intervals in the X-axis direction (hereinafter referred to as "X-axis directional scale mark group") along the X-axis directional numerical value group extracted in step S12. Similarly, the calibration information generation processor 264 extracts a scale mark group existing at regular intervals in the Y-axis direction (hereinafter referred to as "Y-axis directional scale mark group") along the Y-axis directional numerical value group extracted in step S12. In the meantime, the scale marks include, for instance, a mark of a predetermined shape, and a straight line defined by a specific length. Incidentally, a plurality of X-axis directional scale mark groups and Y-axis directional scale mark groups may be extracted.

In addition, when a mark, which is different from the extracted scale marks, exists on a straight line (an extension of a straight line) connecting the extracted scale marks, the calibration information generation processor 264 extracts this mark as a supplementary mark. In this case, by presetting a supplementary mark existing for the extracted scale marks, it becomes possible to extract a proper supplementary mark. For example, if extracted supplementary marks are present at regular intervals, it is highly possible that the scale marks extracted by the calibration information generation processor 264 are scale marks for representing, for instance, an intravital conversion distance. Incidentally, a supplementary mark group existing on a straight line connecting the X-axis directional scale mark group is referred to as "X-axis directional supplementary mark group", and a supplementary mark group existing on a straight line connecting the Y-axis directional scale mark group is referred to as "Y-axis directional supplementary mark group".

The calibration information generation processor 264 stores intervals of extracted scale marks (the interval of the X-axis directional scale mark group and the interval of the Y-axis directional scale mark group), for example, in the inside of this calibration information generation processor 264 (step S14). Incidentally, the interval of the X-axis directional scale mark group includes the number of pixels between neighboring scale marks of the X-axis directional scale mark group. Similarly, the interval of the Y-axis directional scale mark group includes the number of pixels between neighboring scale marks of the Y-axis directional scale mark group.

In addition, the calibration information generation processor 264 stores the positions (X coordinate, Y coordinate) of marks existing at both ends in the selected image data, among the extracted scale marks and supplementary marks. Specifically, the position of a mark existing on the leftmost side and the position of a mark existing on the rightmost side (hereinafter referred to as "X-axis directional both-end positions) of the X-axis directional scale mark group and supplementary mark group are stored. Similarly, the position of a mark existing on the uppermost side and the position of a mark existing on the lowermost side (hereinafter referred to as "Y-axis directional both-end positions) of the Y-axis directional scale mark group and supplementary mark group are stored.

In the meantime, in the description below, a combination pattern of the X-axis directional numerical value group extracted in step S12 and X-axis directional scale mark group (and supplementary mark group) extracted in step S13 is referred to as "X-axis directional pattern". Similarly, a combination pattern of the Y-axis directional numerical value group extracted in step S12 and Y-axis directional scale mark group (and supplementary mark group) extracted in step S13 is referred to as "Y-axis directional pattern". In addition, as described above, there is a case in which a plurality of X-axis directional numerical value groups and scale mark groups and a plurality of Y-axis directional numerical value groups and scale mark groups are extracted. In this case, a plurality of X-axis directional patterns and Y-axis directional patterns exist in the selected image data.

Next, the calibration information generation processor 264 calculates a calibration value (a conversion value per pixel) for each of the X-axis directional pattern and Y-axis directional pattern (step S15). In this case, the calibration information generation processor 264 calculates a calibration value for the X-axis directional pattern (hereinafter referred to as "X-axis directional calibration value") by dividing the difference between neighboring numerical values of the X-axis directional numerical value group by a pixel number (an interval of the X-axis directional scale mark group) between scale marks existing near the respective neighboring numerical values. Similarly, the calibration information generation processor 264 calculates a calibration value for the Y-axis directional pattern (hereinafter referred to as "Y-axis directional calibration value") by dividing the difference between neighboring numerical values of the Y-axis directional numerical value group by a pixel number (an interval of the Y-axis directional scale mark group) between scale marks existing near the respective neighboring numerical values. The calibration values calculated here are used as calibration information at a time of executing a predetermined measurement with respect to an ultrasonic image included in the selected image data.

Incidentally, when a character string representing a unit exists near the X-axis directional pattern, this character string is used as a unit of the X-axis directional calibration value. Similarly, when a character string representing a unit exists near the Y-axis directional pattern, this character string is used as a unit of the Y-axis directional calibration value. On the other hand, when a character string representing a unit does not exist near the X-axis directional or Y-axis directional pattern, a preset unit, for example, is used as the X-axis directional or Y-axis directional calibration value.

The calibration information generation processor 264 specifies a region of an ultrasonic image included in the selected image data (hereinafter, simply referred to as "image region"), based on the X-axis directional both-end positions and Y-axis directional both-end positions stored in the inside of this calibration information generation processor 264 (step S16). This image region is a rectangle (rectangular region) which is set such that, for example, a starting point is set at the X-coordinate of a mark exiting on the leftmost side in the X-axis direction and the Y-coordinate of a mark existing on the uppermost side in the Y-axis direction, an end point is set at the X-coordinate of a mark exiting on the rightmost side in the X-axis direction and the Y-coordinate of a mark existing on the lowermost side in the Y-axis direction, and a straight line connecting the starting point and the end point is set as a diagonal of the rectangle.

In the meantime, when a plurality of X-axis directional patterns and Y-axis directional patterns exit in the selected image data, as described above, an image region is specified with respect to each combination of the X-axis directional pattern and Y-axis directional pattern (both-end positions of these patterns) which are in contact with each other (i.e. have a common part).

The calibration information generation processor 264 generates calibration information including the X-axis directional calibration value and Y-axis directional calibration value with respect to the image region specified in step S16 (i.e. the combination of the X-axis directional pattern and Y-axis directional pattern).

The calibration information generated in the calibration information generation process is set in the inside of the image management processor 262 as additional information of the selected image data, as described above. In this manner, with calibration information being set in the inside of the image management processor 262, this calibration information can be used at a time of executing a predetermined measurement with respect to the ultrasonic image included in the selected image data.

Hereinafter, referring to FIG. 5 to FIG. 7, the calibration information generation process in the present embodiment is concretely described.

Figure 5:
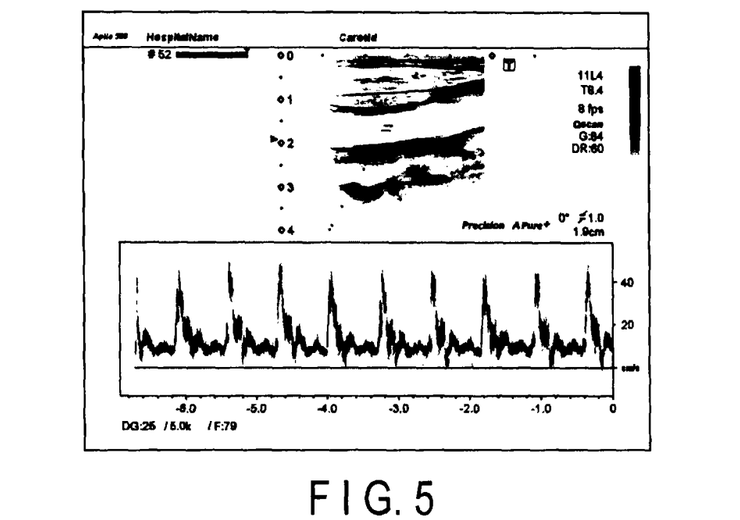
FIG. 5 is a view illustrating an example of image data selected by an operator, among image data stored in a database 25.

FIG. 5 illustrates an example of image data (selected image data) selected by an operator, among image data stored in the database 25. Incidentally, the selected image data illustrated in FIG. 5 is image data at a time when two ultrasonic images are simultaneously displayed on the monitor 14. An ultrasonic image, which exists in an upper part of FIG. 5, is a B mode image. An ultrasonic image, which exists in a lower part of FIG. 5, is a Doppler mode image.

In the calibration information generation process, a binarization process is executed on the selected image data. FIG. 6 illustrates an example of a result of the binarization process executed on the image data shown in FIG. 5. According to the selected image data illustrated in FIG. 6, compared to the selected image data illustrated in FIG. 5, numerical values and scale marks existing in the selected image data become easier to recognize.

Next, an X-axis directional numerical value group and a Y-axis directional numerical value group, which exist in the selected image data (the selected image data that was subjected to the binarization process), are extracted.

Figure 6:
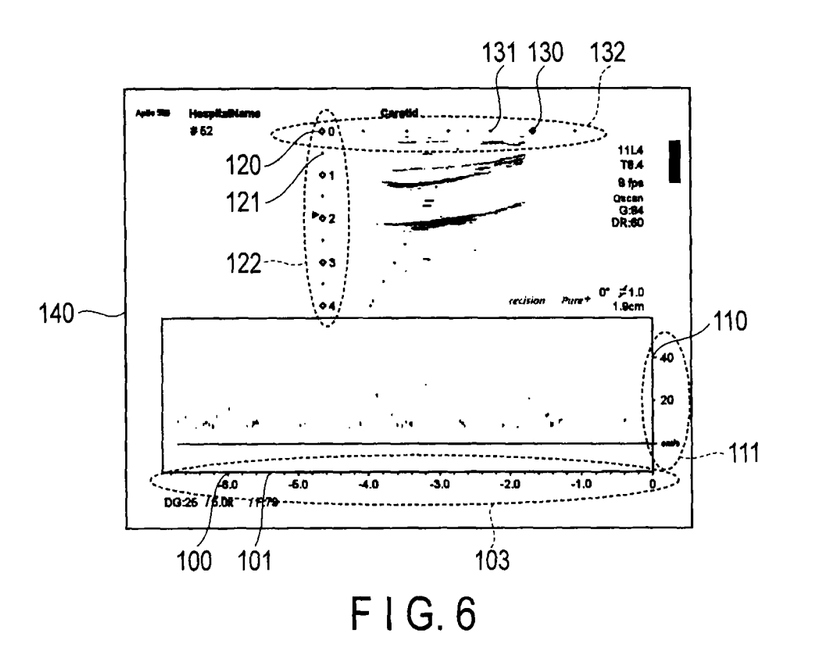
FIG. 6 is a view illustrating an example of a result of a binarization process executed on the image data shown in FIG. 5.

In this case, as the X-axis directional numerical value group, "−6.0", "−5.0", "−4.0", "−3.0", "−2.0", "−1.0", and "0", which exist in a lower part of the selected image data illustrated in FIG. 6, are extracted. On the other hand, as the Y-axis directional numerical value group, "40" and "20", which exist in a right part of the selected image data illustrated in FIG. 6, are extracted. Furthermore, as the Y-axis directional numerical value group, "0", "1", "2", "3" and "4", which exist near an upper middle part of the selected image data illustrated in FIG. 6, are extracted.

Hereinafter, for convenience' sake, the X-axis directional numerical value group, i.e. "−6.0", "−5.0", "−4.0", "−3.0", "−2.0", "−1.0" and "0", is referred to as "first X-axis directional numerical value group". In addition, for convenience' sake, the Y-axis directional numerical value group, i.e. "40" and "20", is referred to as "first Y-axis directional numerical value group". Similarly, for convenience' sake, the Y-axis directional numerical value group, i.e. "0", "1", "2", "3" and "4", is referred to as "second Y-axis directional numerical value group".

Next, in the selected image data, a scale mark group (hereinafter referred to as "first X-axis directional scale mark group"), which exists near the first X-axis directional numerical value group, is extracted. In this case, in the selected image data illustrated in FIG. 6, as the first X-axis directional scale mark group, for example, a plurality of scale marks including a scale mark 100 existing on the upper side of numerical value "−6.0" are extracted. Incidentally, the first X-axis directional scale mark group also includes scale marks similar to the scale mark 100, which exist near the other numerical values "−5.0", "−4.0", "−3.0", "−2.0", "−1.0", and "0". At this time, a plurality of supplementary marks (hereinafter referred to as "first X-axis directional supplementary mark group"), which include a supplementary mark 101 existing on a straight line (an extension line of a straight line) connecting the first X-axis directional scale mark group, are also extracted. Hereinafter, a combination pattern of the first X-axis directional numerical value group, scale mark group and supplementary mark group is referred to as "first X-axis directional pattern 103" for convenience' sake.

Similarly, in the selected image data, a scale mark group (hereinafter referred to as "first Y-axis directional scale mark group"), which exists near the first Y-axis directional numerical value group, is extracted. In this case, in the selected image data illustrated in FIG. 6, as the first Y-axis directional scale mark group, for example, a plurality of scale marks including a scale mark 110 existing on the left side of numerical value "40" are extracted. Incidentally, the first Y-axis directional scale mark group also includes scale marks similar to the scale mark 110, which exist near the other numerical value "20". Hereinafter, a combination pattern of the first Y-axis directional numerical value group and scale mark group is referred to as "first Y-axis directional pattern 111" for convenience' sake.

Furthermore, in the selected image data, a scale mark group (hereinafter referred to as "second Y-axis directional scale mark group"), which exists near the second Y-axis directional numerical value group, is extracted. In this case, in the selected image data illustrated in FIG. 6, as the second Y-axis directional scale mark group, for example, a plurality of scale marks including a scale mark 120 existing on the left side of numerical value "0" are extracted. Incidentally, the second Y-axis directional scale mark group also includes scale marks similar to the scale mark 120, which exist near the other numerical values "1", "2", "3" and "4". At this time, a plurality of supplementary marks (hereinafter referred to as "second Y-axis directional supplementary mark group"), which include a supplementary mark 121 existing on a straight line connecting the second Y-axis directional scale mark group, are also extracted. Hereinafter, a combination pattern of the second Y-axis directional numerical value group, scale mark group and supplementary mark group is referred to as "second Y-axis directional pattern 122" for convenience' sake.

Here, in the selected image data illustrated in FIG. 6, an X-axis directional numerical value, which corresponds to the above-described second Y-axis directional numerical value group, does not exist. However, there exists an X-axis directional scale mark group (hereinafter referred to as "second X-axis directional scale mark group") which is composed of a scale mark 120 and a scale mark 130 that is similar in shape to the scale mark 120. In this case, in the selected image data, a second X-axis directional scale mark group is extracted. At this time, a plurality of supplementary marks (hereinafter referred to as "second X-axis directional supplementary mark group"), which include a supplementary mark 131 existing on a straight line (an extension line of a straight line) connecting the second X-axis directional scale mark group, are also extracted. Hereinafter, a combination pattern of the second X-axis directional scale mark group and supplementary mark group is referred to as "second X-axis directional pattern 132" for convenience' sake.

Next, the interval of the scale marks in the above-described first X-axis directional pattern 103 is stored in the inside of the calibration information generation processor 264. In this case, the number of pixels between neighboring scale marks (here, scale marks existing on the upper side of, e.g. numerical value "−6.0" and numerical value "−5.0") of the first X-axis directional scale mark group is stored.

Although a detailed description is omitted here, the interval (pixel number) between scale marks is similarly stored with respect to the second X-axis directional pattern, first Y-axis directional pattern 111 and second Y-axis directional pattern 122.

Next, the positions of both ends of the first X-axis directional pattern 103, first Y-axis directional pattern 111, second X-axis directional pattern 132 and second Y-axis directional pattern 122 (hereinafter referred to as "first X-axis directional both-end positions", "first Y-axis directional both-end positions", "second X-axis directional both-end positions", and "second Y-axis directional both-end positions") are stored.

Here, as the second X-axis directional both-end positions, as described above, the positions of marks (scale marks or supplementary marks) existing at both ends in the second X-axis directional pattern 132 are stored. Incidentally, the same applies to the second Y-axis directional both-end positions.

On the other hand, as regards the first X-axis directional both-end positions and first Y-axis directional both-end positions, it is assumed that an exceptional process is executed. If a concrete description is given of the first X-axis directional both-end positions, in the selected image data illustrated in FIG. 6, a straight line connecting the first X-axis directional scale mark group (and supplementary mark group) is depicted. In such a case, it is assumed that the positions of both ends of the straight line connecting the first X-axis directional scale mark group and supplementary mark group are stored. Incidentally, it is assumed that the same applies to the first Y-axis directional both-end positions.

Next, a calibration value for the first X-axis directional pattern 103 (hereinafter referred to as "first X-axis directional calibration value") is calculated. This first X-axis directional calibration value is calculated by dividing the difference between neighboring numerical values (in this case, for example, numerical value "−6.0" and numerical value "−5.0") of the above-described first X-axis directional numerical value group by the interval (pixel number) between scale marks in the first X-axis directional pattern 103 (scale marks existing near the respective neighboring numerical values). Here, in the selected image data illustrated in FIG. 6, a character string representing a unit does not exist near the first X-axis directional pattern. In this case, since the X-axis direction represents a time axis in many cases, the unit of the first X-axis directional calibration values is set to be "sec/pix".

In addition, like the above-described first X-axis directional calibration value, a calibration value for the first Y-axis directional pattern (hereinafter referred to as "first Y-axis directional calibration value") is calculated. Here, in the selected image data illustrated in FIG. 6, a character string "cm/sec" representing a unit exists near the first Y-axis directional pattern. Thus, the unit of the first Y-axis directional calibration values is set to be "cm/sec·pix". Incidentally, when the unit of Y axis is "cm/sec·pix", the unit of the corresponding X axis is, in many cases, "sec/pix". Accordingly, based on the unit "cm/sec·pix" of the first Y-axis directional calibration value, the unit of the above-described first X-axis directional calibration value may be determined to be "sec/pix".

In addition, like the above-described first X-axis directional calibration value, a calibration value for the second Y-axis directional pattern (hereinafter referred to as "second Y-axis directional calibration value") is calculated. Here, in the selected image data illustrated in FIG. 6, a character string representing a unit does not exist near the second Y-axis directional pattern. In this case, since the Y-axis direction indicates a length a living body or the like in many cases, the unit of the second Y-axis directional calibration values is set to be "cm/pix".

On the other hand, as described above, no numerical value exists in the second X-axis direction pattern 132. In this case, the calibration value for the second X-axis directional pattern 132 (hereinafter referred to as "second X-axis directional calibration value") is set to be the same value as the calibration value for the pattern (in this case, the second Y-axis directional pattern 122) which is in contact with the second X-axis directional pattern 132 in the selected image data illustrated in FIG. 6. In addition, since the scale mark 120 is common between the second X-axis directional pattern 132 and second Y-axis directional pattern 122, the unit of the second X-axis directional calibration value is set to be the same as the unit of the second Y-axis directional calibration value.

In the meantime, when no character string representing a unit exists in each pattern, it is possible to adopt such a configuration that the operator is prompted to input the unit. Similarly, when no numerical value exists in each pattern, it is possible to adopt such a configuration that the operator is prompted to input the calibration value for each pattern.

Next, a region (image region) of an ultrasonic image included in the selected image data is specified. In the selected image data illustrated in FIG. 6, two ultrasonic images are included as described above. Here, accordingly, two image regions (hereinafter referred to as "first and second image regions") are specified.

The first image region specified here is a rectangular region formed by the first X-axis directional both-end positions and first Y-axis directional both-end positions. On the other hand, the second image region specified here is a rectangular region formed by the second X-axis directional both-end positions and second Y-axis directional both-end positions.

In the meantime, as illustrated in FIG. 6, when a frame 140 is depicted in the selected image data in association with the first X-axis directional pattern and first Y-axis directional pattern, a region inside the frame 140, for example, may be specified as the first image region by utilizing this frame 140.

In addition, in the selected image data illustrated in FIG. 6, for example, if the second X-axis directional scale mark group and supplementary mark group do not exit and the second image region cannot be specified, a region other than the above-described first image region may be specified as the second image region, or, for example, such a configuration may be adopted that the operator is prompted to input the second image region.

Next, calibration information (hereinafter referred to as "first calibration information") including the first X-axis directional calibration value and first Y-axis directional calibration value is generated. The first calibration information is information which is used at a time of executing a predetermined measurement with respect to the ultrasonic image corresponding to the above-described first image region.

Similarly, calibration information (hereinafter referred to as "second calibration information") including the second X-axis directional calibration value and second Y-axis directional calibration value is generated. The second calibration information is information which is used at a time of executing a predetermined measurement with respect to the ultrasonic image corresponding to the above-described second image region.

In the meantime, the first and second calibration information, which was generated as described above, is set as additional information of the selected image data in the inside of the calibration information generation processor 264.

In addition, the first and second calibration information, together with the selected image data, is displayed on the monitor 14.

Specifically, the first X-axis directional calibration value and first Y-axis directional calibration value (the character strings representing these calibration values), which are included in the first calibration information, and the second X-axis directional calibration value and second Y-axis directional calibration value (the character strings representing these calibration values), which are included in the second calibration information, are displayed together with the selected image data.

Figure 7:
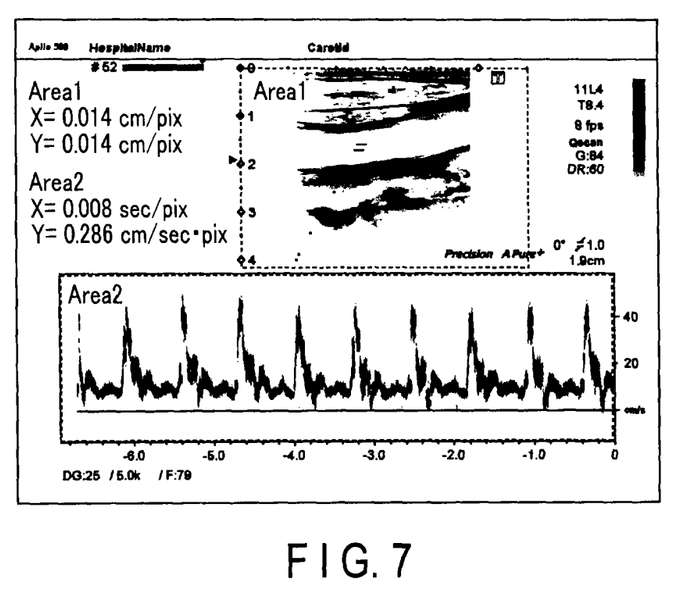
FIG. 7 is a view illustrating an example of a display screen of a monitor 14 at a time when calibration information, together with image data, was displayed.

Here, FIG. 7 illustrates an example of a display screen of the monitor 14 at a time when the first and second calibration information, together with the selected image data, was displayed. Incidentally, in FIG. 7, for convenience's sake, it is assumed that Area1 represents the above-described second image region, and Area2 represents the above-described first image region.

As illustrated in FIG. 7, on the screen of the monitor 14, "x=0.008 sec/pix (first X-axis directional calibration value)" and "y=0.286 cm/sec·pix (first Y-axis directional calibration value)" are displayed as the calibration information of Area2 which represents the above-described first image region.

Similarly, on the screen of the monitor 14, "x=0.014 cm/pix (second X-axis directional calibration value)" and "y=0.014 cm/pix (second Y-axis directional calibration value)" are displayed as the calibration information of Area1 which represents the above-described second image region.

In this manner, since the first and second calibration information is displayed, the operator can easily recognize the calibration values which are applied to each ultrasonic image displayed on the screen.

As has been described above, in the configuration of the present embodiment, based on the positions of the plural numerical values existing in the image data stored in the database 25 and the plural scale marks existing near the respective numerical values, the calibration information including the conversion value (conversion value per pixel) for executing a predetermined measurement with respect to the ultrasonic image included in this image data is generated. By this configuration, for example, exact measurement can be executed by using the calibration information, even with respect to the image data for which no additional information is set. Furthermore, a work load for manually setting the calibration information can be reduced.

In addition, in the present embodiment, even in the case where the image data stored in the database 25 includes a plurality of ultrasonic images, by specifying an image region with respect to each ultrasonic image, proper calibration information can be generated with respect to each image region.

In the meantime, in the present embodiment, the description has been mainly given of the automatic generation of calibration information which is used when a predetermined measurement is executed for the ultrasonic image. However, with a program for this measurement running on the above-described control processor 26, it is also possible to execute a predetermined measurement process on an ultrasonic image included in image data selected by the operator (e.g. a measurement process of an internal organ or diseased part, blood flow velocity, etc. displayed on the ultrasonic image), for example, based on marks (caliper) for measurement set by the operator and the calibration information set as additional information, on the ultrasonic diagnosis apparatus according to the present embodiment.

In this case, in the present embodiment, since the regions (first and second image regions) of the respective ultrasonic images included in the above-described image data are specified, it is also possible to execute a process of detecting an error, for instance, in such a case that the marks for measurement set by the operator fall out of a predetermined region.

Incidentally, in this embodiment, the description has been given on the assumption that the calibration information is generated in the apparatus body 11. However, the calibration information may be generated, for example, in a medical image processing apparatus on the outside of the ultrasonic diagnosis apparatus.

(Modification 1)

In the above, for example, as illustrated in FIG. 5 and FIG. 6, the description has been given of the method of generating calibration information in the case where both the numerical values (character strings) and the scale marks are included in the selected image data. In Modification 1, a description is given of a method of generating calibration information in the case where numerical values (character strings) are not included in the selected image data, and only scale marks are included in the selected image data.

Figure 8:
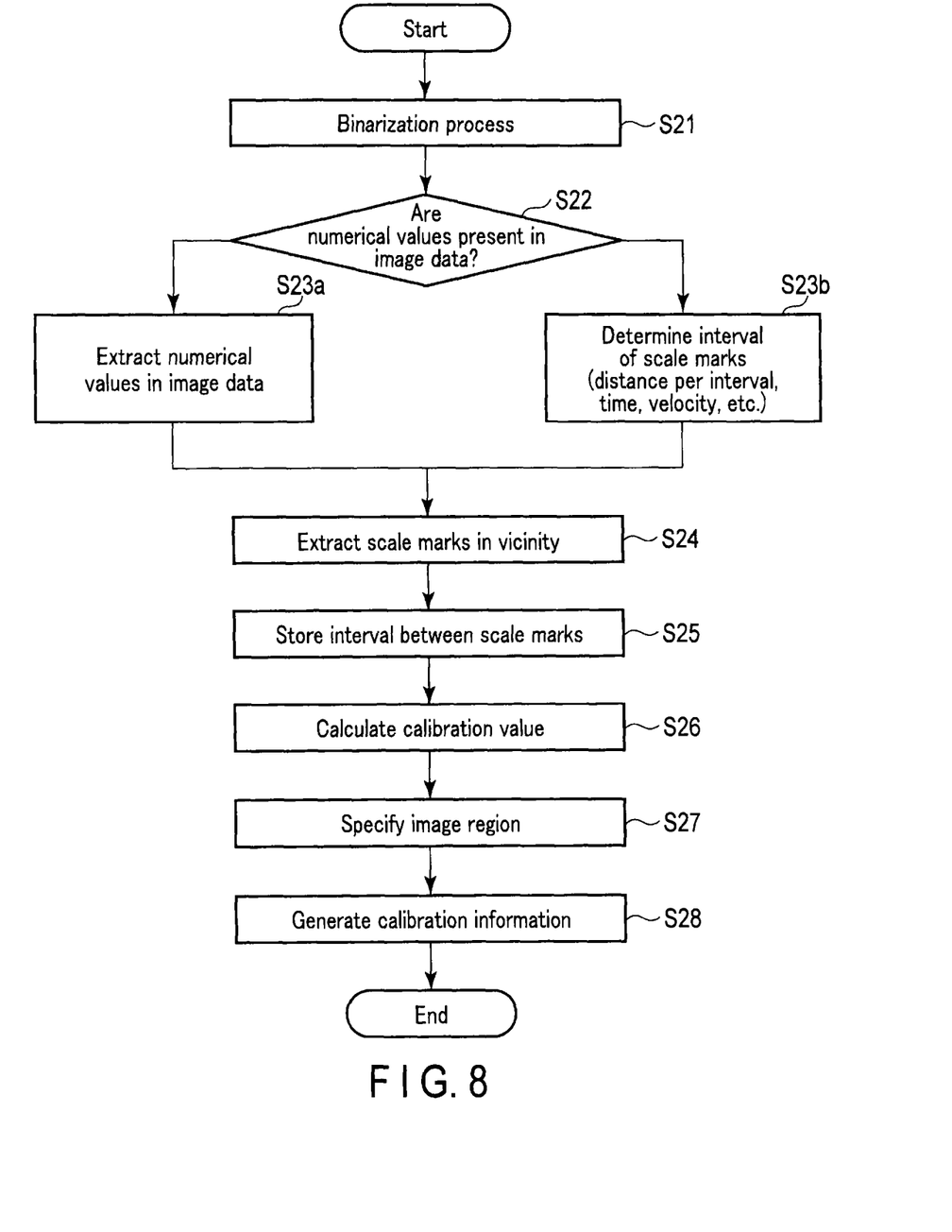
FIG. 8 is a flowchart illustrating a flow of a generation method of calibration information according to Modification 1.

FIG. 8 is a flowchart illustrating a flow of a generation method of calibration information according to Modification 1. Incidentally, the flowchart illustrated in FIG. 8 differs from the flowchart illustrated in FIG. 4 in that steps S22 and S23 are added.

If a binarization process is executed on the acquired selected image data (step S21), the calibration information generation processor 264 determines whether numerical values exist in the selected image data (step S22). If it is determined that numerical values exist in the selected image data, the calibration information generation processor 264 executes, in steps S23*a* to S28, the same process as in the above-described steps S12 to S17.

On the other hand, if it is determined that numerical values do not exist in the selected image data, the control processor 26 displays, for example, on the monitor 14, such a message that "Numerical values indicating the interval of scale marks (distance per interval, time, velocity, etc.) do not exist on the selected image. Input numerical values for determining the interval of scale marks (distance per interval, time, velocity, etc.)." Responding to this message, the user inputs desired numerical values from the input device 13. The calibration information generation processor 264 determines the interval of scale marks (distance per interval, time, velocity, etc.) by using the input numerical values (step S23*b*), and executes the process of steps S24 to S28.

According to Modification 1, even in the case where numerical values are not included in the selected image data and only scale marks are included in the selected image data, calibration information can easily and quickly be generated. Incidentally, in the configuration of Modification 1, in step S23*b*, numerical values for determining the unit of scale marks are input by a manual operation of the user. However, the method is not restricted to this example. From the standpoint of reducing an input work load on the user, the user may select desired numerical values, for example, from among a plurality of preset numerical values. Besides, numerical values for determining the unit of scale marks may be set by using default values which are preset in the apparatus.

(Modification 2)

The generation method of calibration information illustrated in FIG. 4 and FIG. 8 has been described as being executed in such an order that, after the selected image data is subjected to the binarization process, the numerical values in the image are extracted, and the scale marks near them are extracted. However, the method is not restricted to this example. After the scale marks in the binarized selected image are extracted, the numerical values near them may be extracted.

(Modification 3)

In step S13 of FIG. 4 and step 24 of FIG. 8, a typical extraction process of scale marks was described. Meanwhile, for example, when an ultrasonic image is a Doppler waveform, there exists character information inherent to the Doppler mode, such as a unit of velocity of cm/s (m/s), etc., and numerical values (time instants) of "0, −1, −2, . . . ". Such inherent character information may be extracted, scale marks existing near this information may be extracted as a baseline of the Doppler waveform, and calibration information may be generated by using this.

(Second Embodiment)

In an ultrasonic diagnosis apparatus according to a second embodiment, in addition to the calculation of the calibration values, calibration information including an imaging mode of an ultrasonic image included in the selected image is generated and presented.

Figure 9:
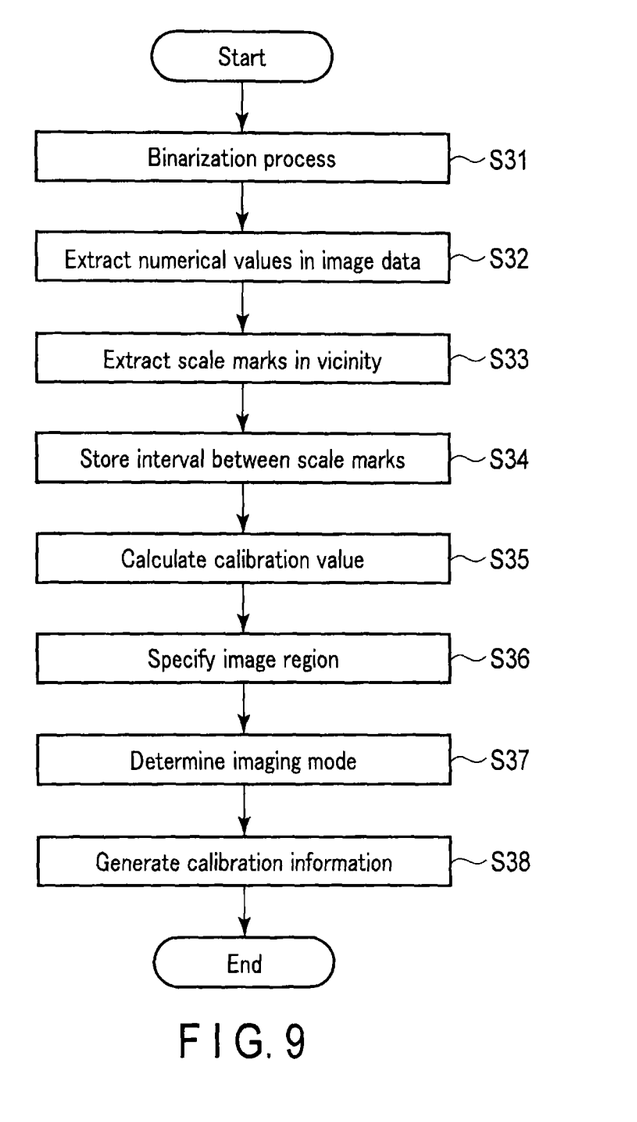
FIG. 9 is a flowchart illustrating a flow of a generation method of calibration information according to a second embodiment.

FIG. 9 is a flowchart illustrating a flow of a generation method of calibration information according to the second embodiment. Incidentally, the flowchart illustrated in FIG. 9 differs from the flowchart illustrated in FIG. 4 in that a process of step S37 is added.

For example, the same process as in steps S11 to S16 illustrated in FIG. 4 is executed in steps S31 to S36 illustrated in FIG. 8. Thereafter, the calibration information generation processor 264 determines an imaging mode of each ultrasonic image included in the image data, by using the numerical value (character string) information extracted in step S32 and the calibration value (physical unit per pixel) calculated in step S35.

For example, if character information inherent to the Doppler mode, such as the unit of velocity of cm/s (m/s), etc., is included in the numerical values extracted in step S35, and character information inherent to the Doppler mode, such as numerical values (time instants) of "0, −1, −2, . . . ", are included in the numerical values extracted in step S32, the calibration information generation processor 264 determines that the imaging mode of the ultrasonic image, to which these numerical values are allocated, is the Doppler mode.

In addition, if the calibration values calculated in step S35 are equal between the X axis and Y axis (i.e. if the scale of numerical values is equal between the X axis and Y axis), the calibration information generation processor 264 determines that the ultrasonic image corresponding to the calibration values is a B mode. On the other hand, if the calibration values calculated in step S35 do not agree between the X axis and Y axis (i.e. if the scale of numerical values is different between the X axis and Y axis), the calibration information generation processor 264 determines that the ultrasonic image corresponding to the calibration values is an M mode (step S37).

In the meantime, when no numerical value is included in the selected image, the imaging mode may also be determined based on a manual operation of the user, etc., like the above-described Modification 1.

The calibration information generation processor 264 generates calibration information including the imaging mode determined in step S37 and the calibration values calculated in step S35, and displays the calibration information in a predetermined mode in which the association with each ultrasonic image included in the selected image is explicitly indicated (step S38).

According to the above-described configuration, the calibration information, which includes not only the calibration values as the physical unit per pixel, but also the imaging mode of each ultrasonic image included in the selected image, can be provided to the user. Accordingly, for example, because of secondary storage data, even if image reproduction is possible by a personal computer but calibration information cannot be reproduced, the calibration information of each ultrasonic image included in the selected image and the imaging mode can be provided, as needed, as the calibration information. As a result, even in the case where an image, which does not conform to specific standards, is handled by a personal computer or a tablet computer, the calibration information can be acquired and used on the spot. As a result, the range of general-purpose uses of medical images can be increased, contributing to an improvement in the quality of diagnosis with imaging, and medical services.

The above described "processor" means, for example, a central processing unit (CPU), a graphics processing unit (GPU), an application specific integrated circuit (ASIC), a programmable logical device (e.g., a simple programmable logic device (SPLD), a complex programmable logic device (CPLD), and a field programmable gate array (FPGA)), or the like.

Note that programs may be directly incorporated in processing circuitry instead that programs are stored in storage memory 12. In this case, the processing circuitry reads programs incorporated in circuitry and executes the programs to realize predetermined functions.

Each function (each component) in the present embodiment is not necessary to be corresponded to a single processing circuit and may be realized by a plurality of processing circuits. To the contrary, for example, at least two functions (at least two components) may be realized by a single processing circuit. Further, a plurality of functions (a plurality of components) may be realized by a single processing circuit.

While certain embodiments of the invention have been described, these embodiments have been presented by way of example only, and are not intended to limit the scope of the invention. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An ultrasonic diagnosis apparatus, comprising:
an ultrasonic probe;
an image generating processor configured to generate an ultrasonic image, based on an echo signal which is obtained through the ultrasonic probe;
a monitor configured to display the ultrasonic image;
a memory configured to store image data, the image data including the ultrasonic image displayed on a screen of the monitor and at least one scale mark with respect to the ultrasonic image;
a calibration information generation processor configured to determine whether a plurality of numerical values exist near the at least one scale mark, and generate, when it is determined that the plurality of numerical values exist, calibration information based on the plurality of numerical values and the at least one scale mark, the calibration information including a conversion value for performing a predetermined measurement with respect to the ultrasonic image included in the image data; and
a control processor configured to control the monitor to display the ultrasonic image in accordance with the calibration information.

2. The ultrasonic diagnosis apparatus of claim 1, wherein the calibration information generation processor is further configured to generate, when it is determined that the plurality of numerical values do not exist near the at least one scale mark, the calibration information, based on numerical values which are input through an input interface.

3. The ultrasonic diagnosis apparatus of claim 1, wherein the calibration information generation processor is further configured to generate, when it is determined that the plurality of numerical values do not exist near the at least one scale mark, the calibration information, based on preset numerical values.

4. The ultrasonic diagnosis apparatus of claim 1, wherein the calibration information generation processor is further configured to determine an imaging mode of the ultrasonic image included in the image data, based on the at least one scale mark and the plurality of numerical values existing near the at least one scale mark, and to generate the calibration information including the determined imaging mode.

5. The ultrasonic diagnosis apparatus of claim 1, wherein the image data stored in the memory includes a plurality of ultrasonic images, and
the calibration information generation processor is further configured to specify regions of the image data that include the respective ultrasonic images, based on a position of the at least one scale mark, and generate the calibration information corresponding to each of the regions.

6. The ultrasonic diagnosis apparatus of claim 1, wherein the calibration information generation processor is further configured to
extract a position of a first numerical value group arranged in a row in an X-axis direction in the image data and a position of a first scale mark group existing near each numerical value of the first numerical value group, and calculate a conversion value in the X-axis direction, based on the extracted positions of the first numerical value group and the first scale mark group,
extract a position of a second numerical value group arranged in a row in a Y-axis direction in the image data and a position of a second scale mark group existing near each numerical value of the second numerical value group, and calculate a conversion value in the Y-axis direction, based on the extracted positions of the second numerical value group and the second scale mark group, and generate the calibration information including the calculated conversion value in the X-axis direction and the calculated conversion value in the Y-axis direction.

7. The ultrasonic diagnosis apparatus of claim 6, wherein the calibration information generation processor is further configured to calculate the conversion value in the X-axis direction by dividing a difference between neighboring numerical values of the extracted first numerical value group by a number of pixels between scale marks of the extracted first scale mark group, which exist near the respective neighboring numerical values, and calculate the conversion value in the Y-axis direction by dividing a difference between neighboring numerical values of the extracted second numerical value group by a number of pixels between scale marks of the extracted second scale mark group, which exist near the respective neighboring numerical values.

8. The ultrasonic diagnosis apparatus of claim 1, wherein the calibration information generation processor is further configured to set a character string representing a unit, which exists near the at least one scale mark, to be a unit of the conversion value.

9. The ultrasonic diagnosis apparatus of claim 1, wherein the calibration information generation processor is further configured to set a preset unit to be a unit of the conversion value, when a character string representing a unit does not exist near the at least one scale mark.

10. The ultrasonic diagnosis apparatus of claim 1, wherein the generated calibration information, together with the image data, is displayed on the monitor.

11. The ultrasonic diagnosis apparatus of claim 1, further comprising a measurement processor configured to execute a predetermined measurement process with respect to the ultrasonic image included in the image data, by using the conversion value included in the generated calibration information.

12. The ultrasonic diagnosis apparatus of claim 1, wherein the calibration information generation processor is further configured to set a character string representing a unit, which exists near the at least one scale mark, to be a unit of the conversion value.

13. A medical image processing apparatus, comprising:

a memory configured to store image data, the image data including a medical image displayed on a screen of a monitor and at least one scale mark with respect to the medical image; and a calibration information generation processor configured to determine whether a plurality of numerical values exist near the at least one scale mark, and generate, when it is determined that the plurality of numerical values exist, calibration information based on the plurality of numerical values and the at least one scale mark, the calibration information including a conversion value for performing a predetermined measurement with respect to the medical image included in the image data; and a control processor configured to control the monitor to display the medical image in accordance with the calibration information.

14. A medical image processing method, comprising:

displaying a medical image and at least one scale mark with respect to the medical image on a screen of a monitor;

determining whether a plurality of numerical values exist near the at least one scale mark;

generating, when it is determined that the plurality of numerical values exist, calibration information based on the plurality of numerical values and the at least one scale mark, the calibration information including a conversion value for performing a predetermined measurement with respect to the medical image; and controlling the monitor to display the medical image in accordance with the calibration information.

* * * * *